Figure 1:
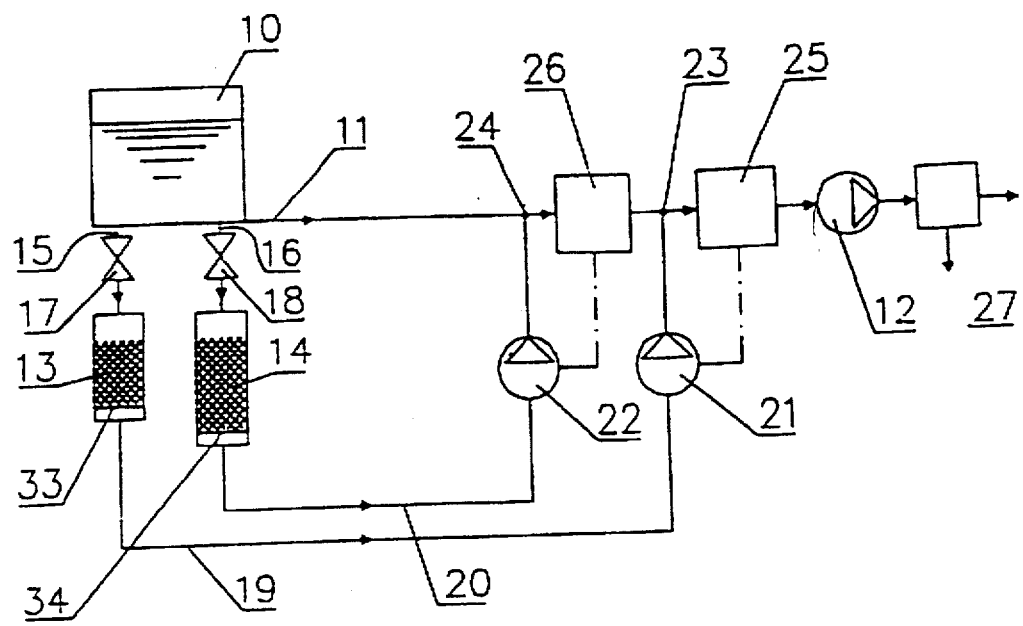

United States Patent [19]
Chevallet et al.

[11] Patent Number: 5,727,877
[45] Date of Patent: Mar. 17, 1998

[54] METHOD FOR PREPARING SOLUTIONS FOR MEDICAL USE

[75] Inventors: Jacques Chevallet, Serezin Du Rhone; Jacques Burtin, Feyzin; Jacques Gauckler, Lyons, all of France

[73] Assignee: Hospal Industrie, France

[21] Appl. No.: 467,455

[22] Filed: Jun. 6, 1995

Related U.S. Application Data

[62] Division of Ser. No. 124,459, Sep. 22, 1993, Pat. No. 5,460,446, which is a continuation of Ser. No. 528,072, May 23, 1990, abandoned.

[30] Foreign Application Priority Data

| May 29, 1989 | [FR] | France | 89 07272 |
| May 29, 1989 | [FR] | France | 89 07273 |
| May 29, 1989 | [FR] | France | 89 07274 |

[51] Int. Cl.⁶ .................. B01F 15/02; B01F 3/12
[52] U.S. Cl. .................. 366/132; 366/137; 366/163.1; 366/182.1
[58] Field of Search .................. 366/132, 136, 366/137, 151, 152, 159, 163.1, 139, 101, 182.2, 348, 182.1; 422/255, 278, 261, 274, 282, 283, 292, 234, 264, 263; 222/152; 137/268, 563, 5, 88, 93, 205, 144, 142; 604/27, 29, 82, 83, 84

[56] References Cited

U.S. PATENT DOCUMENTS

| 1,592,126 | 7/1926 | Paige ...................... 422/261 |
| 1,946,474 | 2/1934 | Banks et al. . |
| 2,135,969 | 11/1938 | Donaldson . |
| 2,820,701 | 1/1958 | Leslie . |
| 3,056,500 | 10/1962 | Carter . |
| 3,244,407 | 4/1966 | Obergfell et al. . |
| 3,266,870 | 8/1966 | Cianflone, Jr. . |
| 3,386,808 | 6/1968 | Handeland . |
| 3,474,817 | 10/1969 | Bates et al. . |
| 3,539,116 | 11/1970 | Podmore . |
| 3,595,395 | 7/1971 | Lorenzen . |
| 3,772,193 | 11/1973 | Nelli et al. ...................... 422/261 |
| 3,820,014 | 6/1974 | Ludt . |
| 4,045,004 | 8/1977 | Berger . |
| 4,202,760 | 5/1980 | Storey et al. . |
| 4,250,910 | 2/1981 | King . |
| 4,293,409 | 10/1981 | Reide et al. . |
| 4,299,501 | 11/1981 | Patil et al. . |
| 4,339,232 | 7/1982 | Campbell . |
| 4,339,332 | 7/1982 | Jasperson . |
| 4,395,130 | 7/1983 | Kutowy . |
| 4,482,704 | 11/1984 | Luetzelschwab . |
| 4,498,784 | 2/1985 | Bernhardsson et al. . |
| 4,580,904 | 4/1986 | Hacheney . |
| 4,664,891 | 5/1987 | Cosentino et al. . |
| 4,734,198 | 3/1988 | Harm et al. . |
| 4,784,495 | 11/1988 | Jonsson et al. . |
| 4,857,355 | 8/1989 | Gregg . |
| 4,908,190 | 3/1990 | Maglio et al. . |
| 5,053,206 | 10/1991 | Maglio et al. . |

FOREIGN PATENT DOCUMENTS

| 0 278 100 | 8/1988 | European Pat. Off. . |
| 2 517 984 | 12/1981 | France . |
| 2 569 560 | 3/1986 | France . |
| 2 114 122 | 3/1971 | Germany . |

*Primary Examiner*—Tony G. Soohoo
*Attorney, Agent, or Firm*—Finnegan, Henderson, Farabow, Garrett & Dunner L.L.P.

[57] ABSTRACT

A main line for delivering a medical solution is connected at one end to a source of liquid. A secondary line is connected at two locations to the main line, bypassing a portion of the main line. A reservoir containing a particulate product is located in the secondary line. During a priming step, liquid is pumped to the reservoir in order to pressurize the reservoir and fill the reservoir to sufficiently immerse the particulate product. This priming step prevents the formation of agglomerates and preferential paths through particulate product. After the reservoir is primed, a fraction of liquid flowing through the main line is diverted into the reservoir and then routed back to the main line to introduce a solution of liquid and particulate product into the main line.

8 Claims, 2 Drawing Sheets

METHOD FOR PREPARING SOLUTIONS FOR MEDICAL USE

This is a divisional of application Ser. No. 08/124,459, filed Sep. 22, 1993, now U.S. Pat. No. 5,460,446, which is a continuation application under 37 C.F.R. § 1.60 of U.S. application Ser. No. 07/528,072 filed May 23, 1990, now abandoned.

The present invention concerns a device for preparing solutions for medical use by mixing a liquid with at least one powdered or crystallized salt. These solutions may be used in particular for haemodialysis, haemofiltration or haemodiafiltration. Such a device allows the on-line preparation of the dialysis liquid necessary for haemodialysis or for haemodiafiltration or of substitute liquids for the blood ultrafiltrate taken from the patient, required for haemofiltration or haemodiafiltration.

A device is known from the European Patent Application 278 100 for preparing a solution for medical use from water and at least one powdered salt comprising in particular:

a main line having a first end connected to a source of water and a second end for delivering the solution;

at least one secondary line joined as a by-pass to the main line, this secondary line comprising a reservoir containing a powdered salt and having an inlet opening and an outlet opening preferably situated respectively at a high point and a low point of the reservoir;

means for causing the liquid to circulate in the lines.

The set of the lines is at atmospheric pressure.

With this arrangement, it has been noted that the water thus circulating from top to bottom in the reservoir has a tendency to create preferred paths in the powdered salt, and that as the salt is humidified, it forms local agglomerates which are relatively difficult to dissolve. These two phenomena—the creation of preferred paths and the formation of agglomerates—are unwelcome in that they prevent the regular and complete dissolution of the salt necessary to proper progress in preparing an on-line solution.

The object of the present invention is thus a device for preparing a solution for medical use which allows a steady dissolution of the salt irrespective of its coefficient of solubility.

To attain this object, provision is made in accordance with the invention, for a device of the type mentioned above, comprising means for immersing the powdered (or crystallized) salt in the salt reservoir.

Because of this arrangement, the salt remains permanently in the fractional state and the solution which is drawn off from the reservoir has a substantially constant concentration which is that of saturation in the case of the salts generally used for the preparation of solutions for medical use, sodium chloride and sodium bicarbonate in particular.

According to one mode of embodiment of the invention, the means for producing the immersion of the powdered salt comprise means for obturating the secondary line arranged up-line from the reservoir and pumping means disposed down-line from the reservoir.

Because of this arrangement, it is possible, before proceeding with the initial filling of the lines, to remove the air contained in the reservoir, so that at the time of the initial filling, the reservoir is totally filled with water and subsequently remains filled.

According to another mode of embodiment of the invention, the means for producing the immersion of the powdered salt in the water comprise means for pressurising the reservoir.

Because of this arrangement, the depth of water in the reservoir may be adjusted by regulating the air pressure in the reservoir so that, at the time of the initial filling, the water level is established above the upper surface of the powdered salt.

According to one characteristic of the invention, the secondary line comprises a loop comprising the reservoir and means for causing the liquid to circulate in the loop in a closed circuit.

Because of this arrangement, the flow of the liquid in the loop is independent of the flow in the rest of the device and this flow can be adjusted so that, at any time, irrespective of the coefficient of the solubility of the salt, the solution circulating in the loop is a saturated solution.

According to another characteristic of the invention, the junction point of the main line with the section of the secondary line connected to the inlet opening of the reservoir is situated down-line, in relation to the direction of the circulation of the liquid in the main line, from the junction point of the main line with the secondary line connected to the outlet opening of the reservoir.

This arrangement is particularly advantageous in the case of salts having a low coefficient of solubility since, by allowing recirculation in the secondary line, it has the result of raising the concentration of the liquid circulating in the secondary line.

Other characteristics and advantages of the present invention will emerge on reading the following description given in relation to the attached drawings wherein:

FIG. 1 schematically represents a first mode of embodiment of the device in accordance with the invention.

Figure 2:
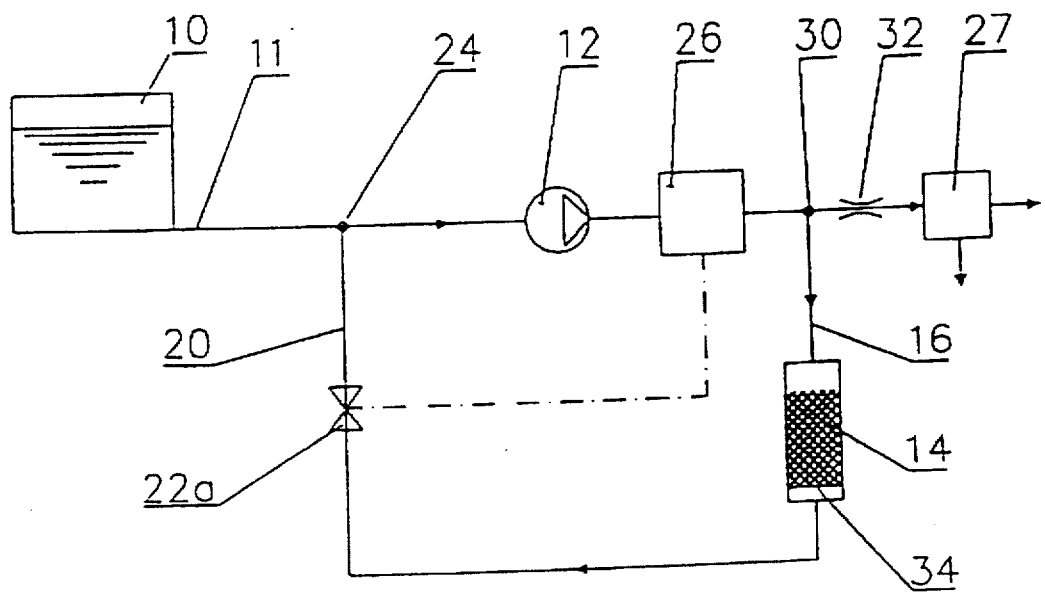
Figure 3:
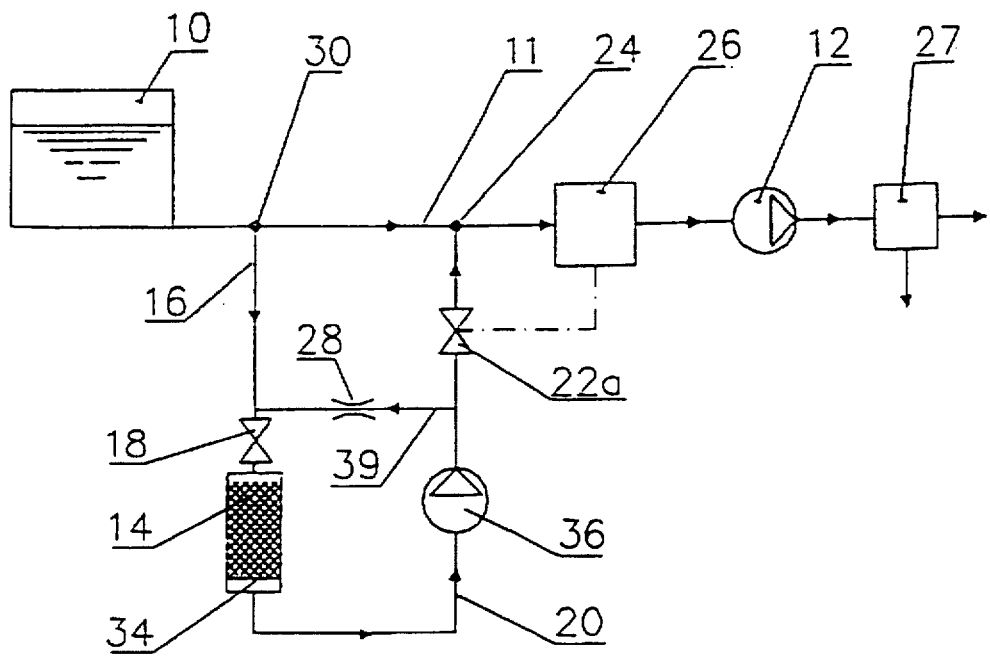
Figure 4:
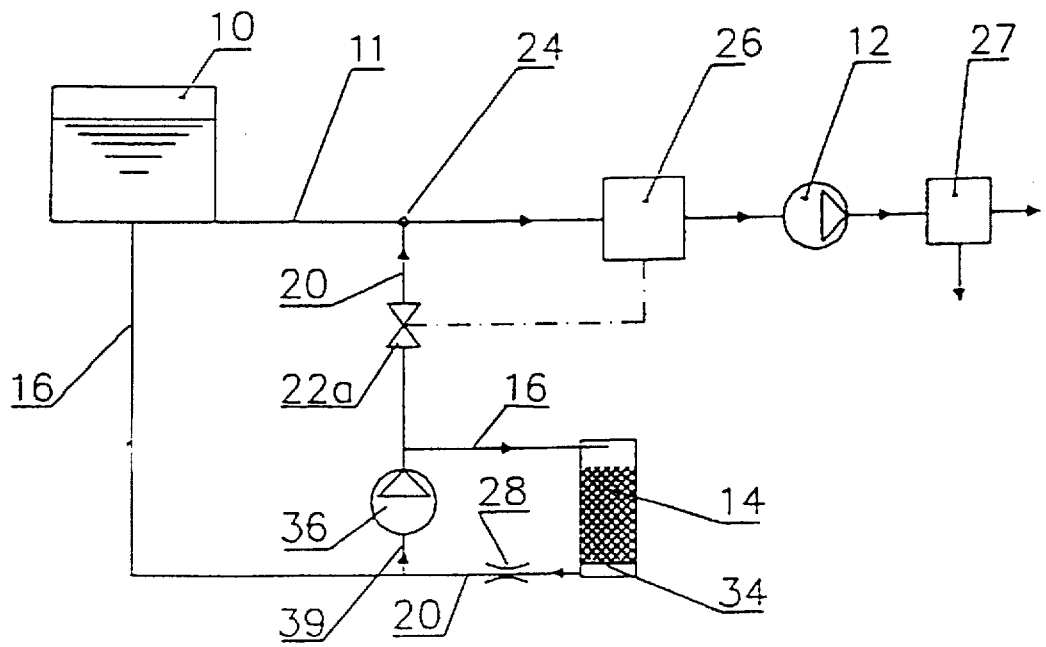

FIG. 2 schematically represents a second mode of embodiment of the device in accordance with the invention;

FIG. 3 schematically represents a third mode of embodiment of the device in accordance with the invention;

FIG. 4 schematically represents a fourth mode of embodiment of the device in accordance with the invention.

Similar elements of the various modes of embodiment of the device in accordance with the invention are designated below by the same reference numerals. Moreover, for greater clarity, only the elements essential for the comprehension of the present invention have been shown in the Figures, by deliberately disregarding all the accessories used in practice, such as devices for heating, degassing, disinfection, cleaning, sterilising, specimen taking etc. which are conventional.

The device represented in FIG. 1 comprises a main line 11 having one end connected to a source 10 of liquid which may be water or a solution and whose other end is connected to a unit 27 for the on-line dispensing and control of the solution for medical use. A pump 12, arranged on the main line, ensures the circulation of the liquid in this line, from the source of the liquid 10 towards the dispensing unit 27. Two secondary lines, of similar structure, are connected in parallel to the main line 11, each of these secondary lines forming a by-pass to the main line.

Each secondary line comprises a reservoir 13 (14) containing a kind of powdered salt (sodium bicarbonate, sodium chloride for example), this reservoir having an inlet opening connected by a tube 15 (16) to the source 10 of the liquid and an outlet opening connected by a tube 19 (20) to the main line 11, at a junction point 23 (24). An obturating device, such as a valve 17 (18) is arranged in the tube 15 (16), that is to say, up-line from the reservoir 13 (14) in relation to the direction of circulation of the liquid in the secondary line, and a pump 21 (22) is arranged on the tube 19 (20), that is to say, down-line from the reservoir 13 (14). As it operates, the pump causes the liquid in the secondary line to circulate from the reservoir 10, towards the junction point 23 (24).

The inlet and outlet openings of the reservoirs 12, 14 are respectively situated at a high point and a low point of these reservoirs. A grille 33 (34) disposed in the bottom portion of each reservoir 13 (14) prevents the undissolved salt from flowing out via the tube 19 (20).

Two elements 25, 26 for measuring the salt concentration of the liquids flowing in the main line 11 are arranged in the duct 11 respectively down-line from the junction points 23, 24. These measuring elements 25, 26 control the pumps 21, 22 according to the instruction values determined by the clinician, whilst the on-line dispensing and control unit 27 shunts the solution produced towards the drain as long as this solution does not have the required concentration of the various salts.

The operation of the device described above is as follows: the initial filling (priming) of the primary and secondary lines with the liquid contained in the reservoir 10 is preceded by a step placing the reservoirs 13, 14 under a partial vacuum. To do this, the secondary lines are obturated up-line from the reservoirs 13, 14 by means of valves 17, 18 and the pumps 21, 22 are operated so as to place the reservoirs 13, 14 at low pressure in relation to the source 10 of liquid (where, for example, a pressure equal to or higher than atmospheric pressure prevails). When the required vacuum level is reached, the valves 17 and 18 are opened and the secondary lines are completely filled with liquid so that the powdered salts contained in the reservoirs 13, 14 are completely immersed and remain so until they are totally dissolved.

FIG. 2 represents a second mode of embodiment of the device in accordance with the invention comprising a main line 11 and a secondary line forming a by-pass to the main line. As before, the main line 11 has its ends respectively connected to a source 10 of liquid (water or solution) and to a unit 27 for the on-line dispensing and control of the solution for medical use.

The secondary line comprises a reservoir 14 for powdered salt having an inlet opening connected via a tube 16 to the main line 11 at a junction point 30, and an outlet opening connected via a tube 20 to the the main line 11, at a junction point 24. The junction point 30 is situated down-line from the junction point 24 with respect to the circulation direction of the liquid in the line 11. The inlet and outlet openings of the reservoir 14 are respectively situated at a high point and a low point of the reservoir.

The circulation of the liquids in the main and secondary lines is produced by a pump 12 arranged in the line 11 between the junction points 24 and 30. The circulation direction of the liquid in the secondary line, along which the liquid partly recirculates in the lines, is imposed by a loss of pressure occurring in the main line 11 down-line from the junction point 30. This pressure loss may be produced by a device not specifically provided for this purpose, the dispensing and control unit 27, for example. It may also be produced by specific means, such as the constriction device 32. It is this loss of pressure which also allows the pressurisation of the reservoir 14 under the action of the pump 12, and hence the filling of the reservoir 14 to the desired level.

Like the earlier device, this device comprises an element 26 for measuring the salt concentration of the solution circulating in the main line. This element is disposed down-line from the junction point 24 and it controls a valve 22a arranged in the secondary line down-line from the reservoir 14 in such a way that the solution circulating in the main line should have the desired salt concentration.

The operation of this device for preparing a solution for medical use is as follow: the initial filling of the main and secondary lines is produced by the operation of the pump 12 which causes the liquid coming from the source 10 to circulate, and pressurises a part of the lines, including the reservoir 14. A proper adjustment of the pressure loss down-line from the junction point 30 by means of the constriction device 32 allows sufficient pressurisation of the reservoir to guarantee the immersion of the salt contained in the reservoir 14 when the device is started. The on-line dispensing and control unit 27 shunts the solution produced towards the drain as long as this solution does not have the required salt concentration.

FIGS. 3 and 4 represent two variants of the device in accordance with the invention, their main common point being that the secondary line comprises a loop comprising the reservoir for powdered salt and means for causing the liquid to circulate in the loop in a closed circuit.

In the device represented in FIG. 3, the loop is closed by a tube 39 connecting the tube 16 to the tube 20 (which, as before, respectively connect the inlet and outlet openings of the reservoir 14 to the main line 11). In the loop thus formed, there are disposed a valve 18 in the tube 16, that is to say, up-line from the reservoir 14, a pump 36 on the tube 20, that is to say, down-line from the reservoir 14, and a constricting device 28 on the tube 39. The measuring element 26 disposed on the main line 11 down-line from the junction point 24 of the tube 20 to the main line controls a valve 22a disposed in the tube 20 down-line from the loop.

The device described above operates as follows: before the main and secondary lines are filled, the valve 18 is closed, the valve 22a is opened and the pump 36 is started so as to create a partial vacuum in the reservoir 14. When the desired vacuum level has been obtained, the value 18 is opened. When the lines are completely filled, the valve 22a is closed and the liquid then circulates in a closed circuit in the loop under the effect of the pump 36 whose delivery is adjusted to ensure that the liquid in the loop is rapidly saturated. The valve 22a is then opened and a portion of the saturated solution contained in the loop flows into the main line 11 where it is mixed with the liquid drawn off from the source 10 by the pump 12, while it is simultaneously replaced in the loop by liquid drawn off by the pump 36 from the source 10 via the tube 16. The function of the constricting element 28 disposed on the tube 39 is to promote the intake of liquid and the emergence of the solution into/out of the loop when the valve 22a is opened. As in the devices described above, the on-line dispensing and control unit 27 shunts the prepared solution towards the drain as long as the salt concentration has not reached the required level.

The device represented in FIG. 4 is different from the one described above in that the secondary line is closed to form a loop by a tube 39 which is a tube section common to the tubes 16 and 20, in which section there is disposed a pump 36 that draws the liquid coming from the source 10 and the solution emerging from the reservoir 14 and delivers it towards the main line 11 and the inlet of the reservoir 14. The loop moreover comprises a constricting element 28 disposed down-line from the reservoir 14 in the tube 20. The measuring element 26 disposed in the main line 11 down-line from the junction point 24 of the tube 20 with the main line controls a valve 22a disposed in the tube 20 down-line from the loop.

The operation of the device described above is as follows: for the initial filling of the lines, the valve 22a is closed and the pumps 36 and 12 are started. The pump 36 fills the secondary line with the liquid from the source 10 whilst pressurising the reservoir 14, thanks to the pressure loss produced by the constricting element 28. As a result of this pressurisation which can be adjusted by any known means, the salt contained in the reservoir is immersed when the filling of the secondary line has been completed. As soon as this filling has been completed, the pump 36 produces the circulation of the liquid in the loop in a closed circuit at a rate of flow chosen so that it should be quickly saturated.

The operation of this device under steady conditions does not differ from that of the device described with reference to FIG. 3.

The present invention is not limited to the examples described above and it can accommodate variants. In particular, in the circuits for preparing the solution comprising several secondary lines, these secondary lines can be joined in series to the main line and not only in parallel as in the mode of embodiment represented in FIG. 1.

We claim:

1. A method for preparing in-line a medical solution in a medical device having a main line with a first end connected to a source of liquid and a second end for delivering the medical solution, the device also including at least one secondary line having a first portion for connecting an inlet of a reservoir containing a soluble particulate product and a gas to the main line at a first connecting point, and having a second portion for connecting an outlet of the reservoir to the main line at a second connecting point, the second connecting point being located between the source and the first connecting point, the method comprising the steps of:

priming the reservoir by pumping liquid through the main line to the reservoir in order to pressurize the reservoir, thereby reducing space in the reservoir occupied by gas and filling the reservoir to at least a first level immersing the particulate product and forming a solution of the particulate product and the liquid;

pumping, after the step of priming, the liquid from the source into the main line;

constricting the main line at a location between the first connecting point and the second end so that liquid flow is restricted at the location when liquid is pumped through the main line; and flowing a fraction of the liquid contained in the main line into the secondary line at the first connecting point to cause solution in the reservoir to flow out of the reservoir and mix with liquid from the source at the second connecting point.

2. The method of claim 1, further comprising the steps of:

sensing a concentration of the particulate product in the solution in the main line;

comparing the sensed concentration to a desired concentration;

adjusting a flow rate of the solution of the particulate product in the secondary line to substantially equalize the sensed concentration with the desired concentration.

3. The method of claim 2, further comprising the step of discarding the solution of the particulate product flowing through the main line at times when the sensed concentration is not substantially equal to the desired concentration.

4. The method of claim 1, further comprising the step of recirculating the solution of the particular product in the secondary line, the main line, and through the reservoir to provide a saturated solution of the particulate product at the second connecting point.

5. The method of claim 1, wherein the step of pumping after the step of priming is accomplished using a pump located in the main line between the first and second connecting points.

6. The method of claim 1, wherein the step of constricting occurs during the step of priming, pumping and flowing.

7. The method of claim 1, wherein the step of constricting comprises permanently constricting the main line at the location between the first connecting point and the second end.

8. A method for preparing in-line a medical solution in a medical device having a main line with a first end connected to a source of liquid and a second end for delivering the medical solution, the main line having a constriction therein, the device also including at least one secondary line having a first portion for connecting an inlet of a reservoir containing a soluble particulate product and a gas to the main line at a first connecting point between the constriction and the source, and having a second portion for connecting an outlet of the reservoir to the main line at a second connecting point, the second connecting point being located between the source and the first connecting point, the method comprising the steps of:

pumping, at a location between the first and second connecting point, the liquid from the source through the main line thereby:

filling the reservoir to at least a first level immersing the particulate product;

pressurizing the reservoir thereby reducing the space in the reservoir occupied by gas, forming a solution of the particulate product and the liquid in the reservoir, flowing the solution through the secondary line, mixing the solution with the liquid from the source; and regulating a flow rate of the solution in the secondary line so that a resulting in-line medical solution has a desired concentration.

* * * * *

UNITED STATES PATENT AND TRADEMARK OFFICE
CERTIFICATE OF CORRECTION

PATENT NO. : 5,727,877
DATED : March 17, 1998
INVENTOR(S) : Jacques Chevallet, et al.

It is certified that error appears in the above-indentified patent and that said Letters Patent is hereby corrected as shown below:

Claim 4, Column 6, line 6, "particular" should read --particulate--.

Signed and Sealed this

Nineteenth Day of May, 1998

Attest:

BRUCE LEHMAN

Attesting Officer

Commissioner of Patents and Trademarks